United States Patent [19]

Esanu

[11] 4,267,181
[45] May 12, 1981

[54] HALOGENO DERIVATIVES OF ISOPROPYLAMINO PYRIMIDINE AND THERAPEUTIC USE

[75] Inventor: Andre Esanu, Paris, France

[73] Assignee: Societe d'Etudes de Produits Chimiques, Paris, France

[21] Appl. No.: 144,761

[22] Filed: Apr. 28, 1980

[30] Foreign Application Priority Data

May 15, 1979 [GB] United Kingdom ............... 16918/79

[51] Int. Cl.³ .................. A61K 31/505; C07D 239/42
[52] U.S. Cl. ..................................... 424/251; 544/330
[58] Field of Search ......................... 544/330; 424/251

[56] References Cited

U.S. PATENT DOCUMENTS

| | | | |
|---|---|---|---|
| 2,436,360 | 2/1948 | Hultquist et al. | 544/330 |
| 2,609,372 | 9/1952 | Ziegler | 544/330 |
| 3,984,414 | 10/1976 | Esanu | 544/330 |
| 4,073,895 | 2/1978 | Esanu | 544/330 |

Primary Examiner—Paul M. Coughlan, Jr.
Attorney, Agent, or Firm—Eyre, Mann, Lucas & Just

[57] ABSTRACT

The invention relates to new isopropylamino pyrimidine halogeno derivatives of the formula:

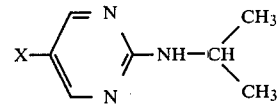

in which X represents a fluorine, a chlorine or a bromine atom. These compounds, when X stands for chlorine or bromine, are prepared by reacting, at room temperature and in stoichiometric proportions, 2-isopropylamino pyrimidine on the appropriate N-halogeno succinimide, in the presence of acetic acid.

2 Claims, No Drawings

HALOGENO DERIVATIVES OF ISOPROPYLAMINO PYRIMIDINE AND THERAPEUTIC USE

The present invention relates to new halogeno derivatives of isopropylamino-pyrimidine which are of interest in the therapeutical field, in particular for the treatment of various neuropathies.

The invention provides 2-isopropylamino-5-halogeno pyrimidines having the general formula:

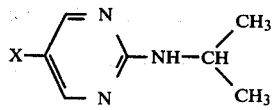

in which X represents a fluorine, chlorine or bromine atom.

Those compounds in which X represents a chlorine or bromine atom may readily be prepared by reacting, at room temperature and in stoichiometric proportions, 2-isopropylamino pyrimidine with N-chloro or bromo-succinimide in the presence of acetic acid. The yield is over 90%.

2-isopropylamino-5-fluoro pyrimidine may be prepared by treating 2-isopropylamino-5-chloro or bromo pyrimidine with potassium fluoride.

The compounds according to the invention are also useful as intermediates for the preparation of other derivatives of 2-isopropylamino pyrimidine such as, for instance, the corresponding hydroxy derivatives. The invention is illustrated by the following examples:

EXAMPLE 1

2-isopropylamino-5-bromo pyrimidine 75 ml of acetic acid, 13.7 g (0.1 mole) of 2-isopropylamino-pyrimidine and 17.8 g (0.1 mole) of N-bromosuccinimide are poured into a 1 liter reaction vessel. The reaction mixture is stirred for 1 hour at room temperature and then poured into iced water. The resultant precipitate is filtered off, washed with water and dried. 20 g (yield 92%) of the title compound was obtained as a white powder melting at 90° C. Elemental analysis showed that the compound had the expected empirical formula of $C_7H_{10}N_3Br$.

EXAMPLE 2

2-isopropylamino-5-chloro pyrimidine

Example 1 was repeated save that the N-bromosuccinimide was replaced by N-chlorosuccinimide. The title compound was obtained as a white powder in a yield of 96%. Elemental analysis showed that the compound had the expected empirical formula of $C_7H_{10}N_3Cl$.

EXAMPLE 3

2-isopropylamino-5-fluoro pyrimidine

Stoichiometric proportions of 2-isopropylamino-5-bromo-pyrimidine, prepared as described in example 1, and potassium fluoride were reacted together for 5 hours. After appropriate working up, the title compound was obtained as a white powder in a yield of 83%. Elemental analysis showed that the compound had the expected empirical formula of $C_7H_{10}N_3F$.

TOXICITY

The acute tocicity (mg/kg of the compounds of the invention was determined on mice i.p. and per os and the values are reported in the following table:

| Route | compound | | |
| --- | --- | --- | --- |
| | Ex. 1 | Ex. 2 | Ex. 3 |
| i.p. | 310 | 325 | 460 |
| per os | 420 | 415 | 615 |

PHARMACOLOGY

The pharmacological activity of the compound of the invention has been researched by the following comparative experimentation undertaken on the regeneration of the sciatic nerve of the male adult rat (Wistar).

A lesion is made on the sciatic nerve of the rats by application of a thermosound at −20° C. for 20 minutes on the nerve. The rats are then treated i.p. by the reference product or by the compounds of the invention for a predetermined duration. At the end of the treatment, the rats are killed, the sciatic nerves are separated and placed in contact with a sery of 70 thin parallel platinum wires (interval 1 mm) and an electric signal applied upstream the lesion point is researched on the platinum wires: the more distant wire where the signal can be collected gives the regenerated length.

For each tested composition and each duration of treatment, a batch of 8 rats is used.

Four compositions have been tested i.p.: Example 1 compound, Example 2 compound, Example 3 compound, all at the i.p. dose of 15 mg/kg and, as a reference, a mixture of vitamins B1 (500 mg/kg), B6 (500 mg/kg) and B12 (5 mg/kg) which is known in the art to be the most effective composition in this field. Controls received no treatment at all. Five batches of 8 animals were used for each duration (7, 11, 14, 17 and 21 days) either for controls or for compounds 1, 2, 3 or reference mixture.

The results of this experimentation are summarized in the following table together with the figures obtained for control animals. The lengths of regenerated nerves are indicated in mm. at the respective day columns as an average value of the lengths measured for all the animals of each batch. When no figure appears (17 and 21 days) this means that the regenerated length exceeded the length of the taken sample.

| Compound and dose i.p. | Duration (days) | | | | |
| --- | --- | --- | --- | --- | --- |
| | 7 | 11 | 14 | 17 | 21 |
| Controls | 5.4 | 10.4 | 13.0 | 17.9 | 23.0 |
| Example 1 10 mg/kg | 6.8 | 14.4 | 26.6 | — | — |
| Example 2 10 mg/kg | 6.7 | 14.4 | 26.2 | — | — |
| Example 3 10 mg/kg | 6.1 | 13.6 | 22.9 | 25.2 | — |
| B1, B6, B12 500 mg/kg, 500 mg/kg and 5 mg/kg | 8.6 | 13.5 | 16.1 | 20.9 | 24.8 |

PRESENTATION—POSOLOGY

These derivatives may be presented in any therapeutically acceptable form and, for instance, in tablets or in gelatine capsules containing 5 mg per dosage unit together with an excipient; for injectable form, the product may be dosed in phials containing at least 1 mg of active ingredient under the form of its hydrochloride dissolved in water. As to the posology for human use, oral administration requires from 30 mg to 1 g per diem whereas injectable form may be administered at doses between 2 mg to 50 mg per diem.

An example of the tablet form is given hereunder:

| Compound of any of the examples | 10 mg |
|---|---|
| Lactose | 70 mg |
| Talc | 15 mg |
| Magnesium stearate | 5 mg |
| | 100 mg |

I claim:

1. New isopropylamino pyrimidine halogeno derivatives of the formula:

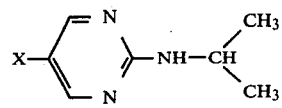

in which X represents a fluorine, a chlorine or a bromine atom.

2. A therapeutic composition of mattter comprising, per dosage unit, from 1 mg to 0.1 g of a compound according to claim 1 together with an appropriate carrier.

* * * * *